United States Patent
Huttner et al.

(10) Patent No.: US 8,728,107 B2
(45) Date of Patent: May 20, 2014

(54) METHOD OF REMOVING CERUMEN OR A FOREIGN BODY FROM AN EAR CANAL AND ARTICULATING CURETTE FOR USE THEREWITH

(75) Inventors: James J. Huttner, Sylvania, OH (US); Josh Noble, Oak Harbor, OH (US)

(73) Assignee: Bionix Development Corporation, Toledo, OH (US)

(*) Notice: Subject to any disclaimer, the term of this patent is extended or adjusted under 35 U.S.C. 154(b) by 0 days.

(21) Appl. No.: 13/453,077

(22) Filed: Apr. 23, 2012

(65) Prior Publication Data
US 2012/0203256 A1   Aug. 9, 2012

Related U.S. Application Data

(63) Continuation of application No. 12/616,253, filed on Nov. 11, 2009, now abandoned.

(60) Provisional application No. 61/199,010, filed on Nov. 12, 2008.

(51) Int. Cl.
*A61F 11/00* (2006.01)

(52) U.S. Cl.
USPC .......................................... 606/162

(58) Field of Classification Search
USPC ............. 606/162, 161, 106; 604/1; D24/133, D24/135, 146–149; 15/172; 30/272.1; 132/218, 136, 317, 318
See application file for complete search history.

(56) References Cited

U.S. PATENT DOCUMENTS 6,074,405 A * 6/2000 Koch ........................... 606/160
2008/0044791 A1 * 2/2008 Tsurukawa et al. ........... 433/141

FOREIGN PATENT DOCUMENTS

WO    WO2007022519    *   2/2007   ................. 600/37

* cited by examiner

*Primary Examiner* — Ryan Severson
*Assistant Examiner* — Anh Dang
(74) *Attorney, Agent, or Firm* — Marshall & Melhorn, LLC

(57) ABSTRACT

A method of removing cerumen or a foreign body from an ear canal utilizes an articulating ear curette.

5 Claims, 4 Drawing Sheets

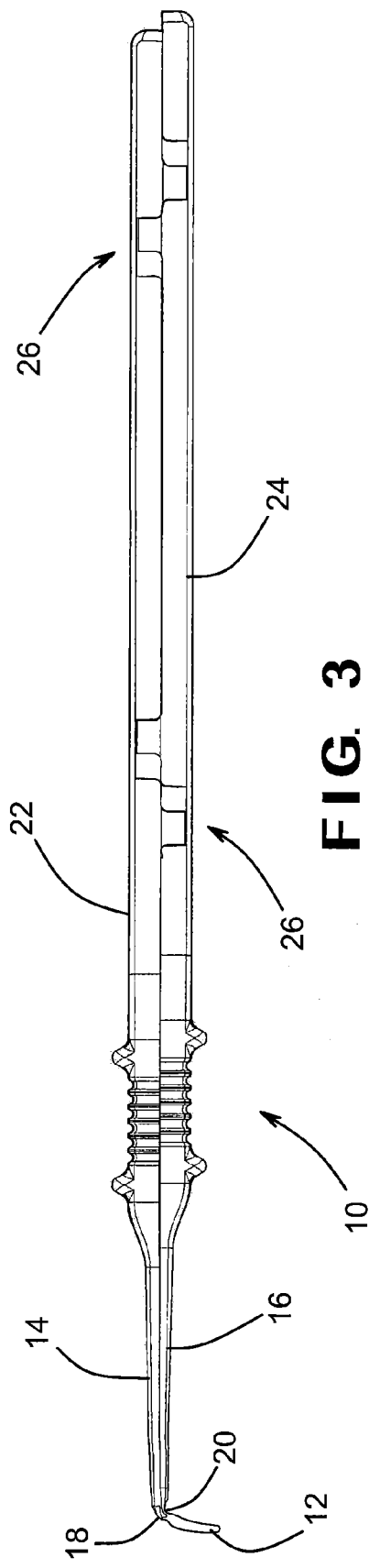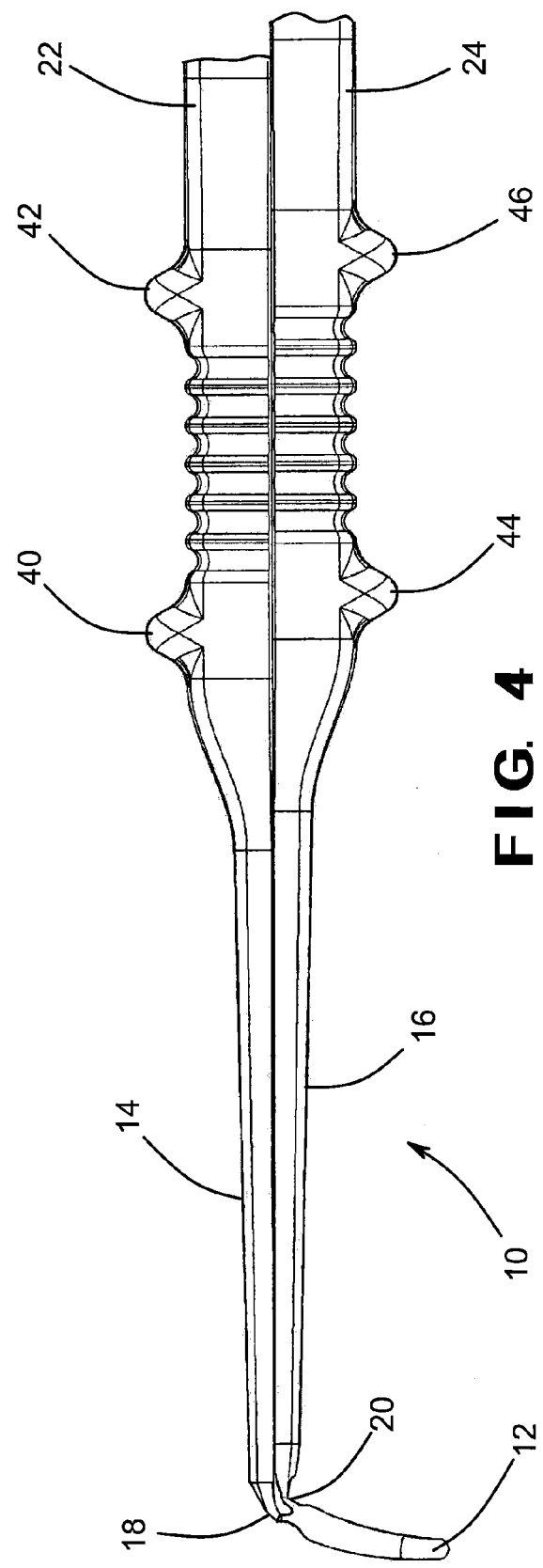
FIG. 3
FIG. 4

METHOD OF REMOVING CERUMEN OR A FOREIGN BODY FROM AN EAR CANAL AND ARTICULATING CURETTE FOR USE THEREWITH

RELATED APPLICATIONS

This application is a continuation application of pending application Ser. No. 12/616,253 filed Nov. 11, 2009, which application claims the benefit, under 35 U.S.C. §119(e), of the provisional application filed Nov. 12, 2008 under 35 U.S.C. §111(b), which was granted Ser. No. 61/199,010. Both applications are hereby incorporated by reference in its entirety.

BACKGROUND OF THE INVENTION

Ear curettes designed for the removal of cerumen from the ear canals of children and adults have been known for some time. Bionix Development Corp. developed the first plastic ear curette, introducing it into the marketplace in 1984. Since then, Bionix has expanded its line of Safe Ear™ Curettes to include seven different tip styles, each designed to meet a particular problem with impacted cerumen encountered in clinical practice.

In 2004, Bionix introduced its Lighted Ear Curette, and has since expanded the line to include six different tip styles. The Lighted Ear Curette (LEC) is constructed of light-conducting polycarbonate plastic that allows light from the attached light source to be transmitted into the ear canal. This serves to illuminate the ear canal, turning what was a blind procedure into one allowing direct observation of the cerumen removal.

Thus far, all of the Bionix ear curettes, both Safe Ear™ Curettes and Lighted Ear Curettes, are static in nature, i.e. the tips, although flexible, are not designed to move during the procedure. This can present a problem when it is desirable to get behind a piece of wax or, in some cases, a foreign body to pull it from the ear canal. In these cases, using a standard ear curette—such as either the Safe Ear™ Curette or LEC—requires the user to push down on the curette with sufficient force to trap the wax or foreign body against the ear canal wall and try to roll it out. This can cause significant pain to the patient, and is often not successful.

In addition, there are moveable graspers and picks that are known to the medical market. One such device, the Quire Mechanical Finger, uses a hinged tip connected to metal actuating arms such that, when the actuating arms slide relative to each other the action causes the tip to swing downward on its hinge. The device also needs a spring mechanism to return the tip to its un-bent position. This requires the user to grasp the device at the spring handle end, distal from the ear canal and in an awkward and unwieldy fashion for the delicate procedure of removing a foreign object from the ear.

BRIEF SUMMARY OF THE INVENTION

To address these problems, we have invented an articulating ear curette, one with a moveable tip that will allow the user to slip the curette tip over or around the wax chunk or foreign body and then manipulate the curette to bend the tip downward (relative to the handle) behind the object to drag it from the ear canal.

The articulating ear curette of the invention comprises a curette tip connected to first and second actuator arms. The curette tip is connected to the first actuator arm through a first molded-in living hinge and to the second actuator arm through a second molded-in living hinge. The actuator arms are slidably connected to one another such that relative movement of the first and second actuator arms in opposite directions causes movement of the tip about the first and second living hinges.

In a further aspect of the invention, a method is provided for removing cerumen or a foreign body from an ear canal utilizing the ear curette of the invention. In accordance with the method, the curette tip is introduced into the ear canal. The ear curette is actuated by forcing the first and second actuator arms in opposite directions, thereby causing movement of the curette tip about the first and second living hinges, the curette tip engaging at least a portion of the cerumen or the foreign body in the ear canal. The curette tip is then withdrawn from the ear canal along with at least a portion of the cerumen or the foreign body.

BRIEF DESCRIPTION OF THE DRAWINGS

The advantages of the invention will become readily apparent to those skilled in the art from the following detailed description of various embodiments when considered in the light of the accompanying drawings, in which:

FIG. 3 is a side view of the curette of FIG. 1 in a flexed position;

FIG. 4 is an enlarged view of an end portion of the curette shown in FIG. 3;

DETAILED DESCRIPTION OF THE INVENTION

It is to be understood that the specific devices and processes illustrated in the attached drawings and described in the following description are simply exemplary embodiments of the inventive concepts defined in the appended claims. Hence, specific dimensions and other physical characteristics relating to the embodiments disclosed herein should not be considered as limiting, unless the claims expressly state otherwise.

The invention is an articulating ear curette that includes a moveable tip. The curette is designed so that by manipulating the handle of the curette, the user can cause the tip of the curette to bend downward, preferably at up to a 90 degree angle relative to the long axis of the curette. This feature is particularly useful in removing chunks of wax and debris including foreign objects from the ear canal. As discussed above, none of the ear curettes known previously in the art exhibit any moving parts, nor do they allow independent movement of the curette tip.

Figure 1:
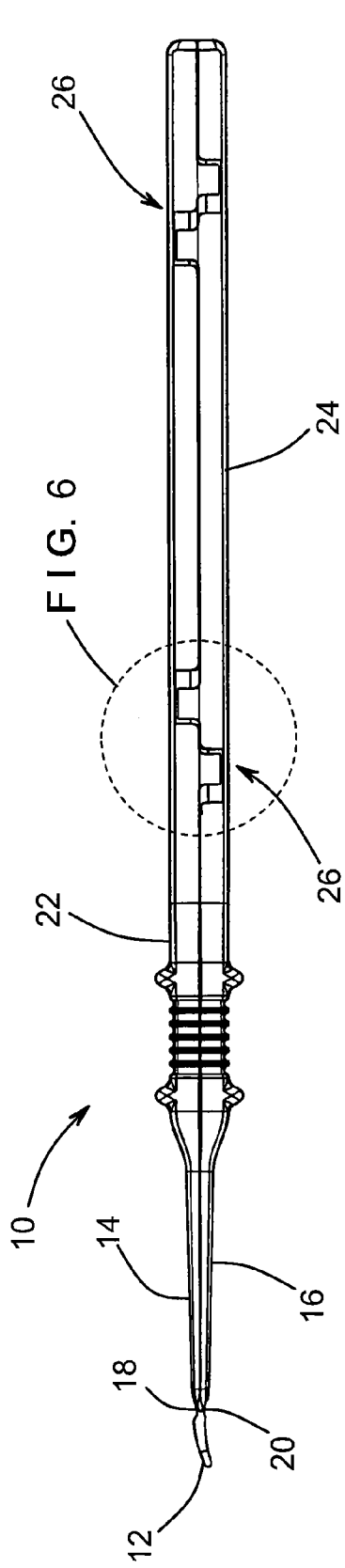
FIG. 1 is a side view of a preferred embodiment of the ear curette of the invention in an unflexed position.

Referring now to the drawings, FIG. 1 shows a preferred embodiment of the articulating ear curette 10 of the invention with a moveable tip 12. The moveable curette tip 12 is connected to first and second actuator arms 14 and 16. The curette tip 12 is connected to the first actuator arm 14 through a first molded-in living hinge 18 and to the second actuator arm 16 through a second molded-in living hinge 20. Preferably, the tip 12 and arms 14, 16 are molded as a one-piece unit from a polymeric material, and the hinges 18, 20 are formed as two thin webs of the material.

The first actuator arm 14 extends away from the tip 12 to form a first handle portion 22, while the second actuator arm 16 extends away from the tip 12 to form a second handle portion 24. The first and second handle portions 22, 24 engage one another in such a manner that allows some amount of relative movement between the first and second handle portions 22, 24, and thus the first and second actuator arms 14, 16 in an axial direction. At the same time, relative movement between the first and second handle portions 22, 24 of the first and second actuator arms 14, 16 in a radial direction is generally prevented.

In a preferred embodiment of the invention, this is accomplished by providing at least one mechanical stop 26 that limits the amount of relative movement between the first and second actuator arms 14, 16 in opposite axial directions. Preferably, there are two or more of the mechanical stops 26. In the most preferred embodiment illustrated in the drawings, four such stops 26 are provided, two spaced apart along the length of the handle portions 22, 24 on each side thereof. Only the two stops 26 on the one side of the handle portions 22, 24 are shown in FIGS. 1 and 3, the opposite side being a mirror image of the side shown.

The one or more mechanical stops 26 are preferably formed by a combination of structures on the handle portions 22, 24. In a preferred embodiment, the mechanical stops are formed by a projection extending from one of the handle portions of one of the second actuator arms that is positioned within a slot formed in the handle portion of the other actuator arm, so that after relative sliding movement of the handle portions of the first and second actuator arms in opposite directions for a desired distance, the projection will abut an end of the slot to stop further such relative movement.

Figure 6:
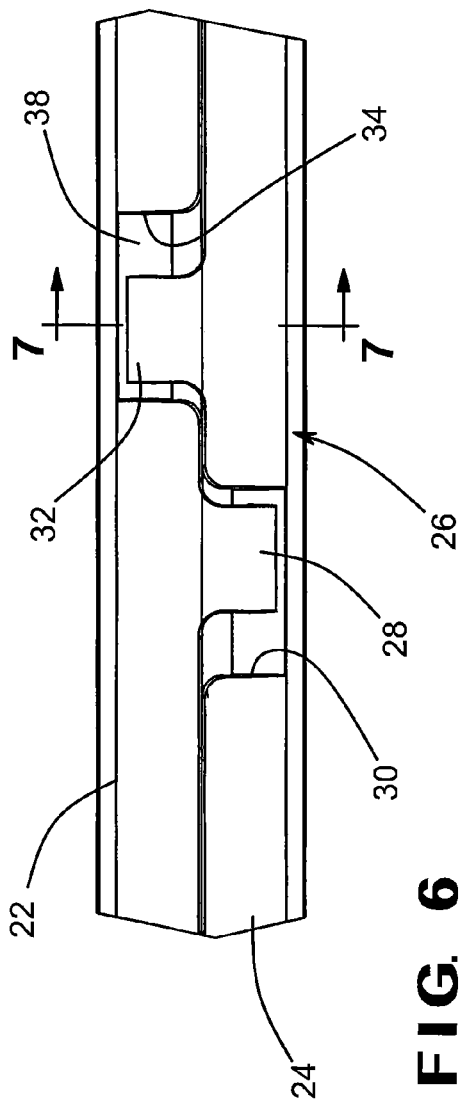
FIG. 6 is an enlarged view of a handle portion of the curette shown in FIG. 1.
Figure 7:
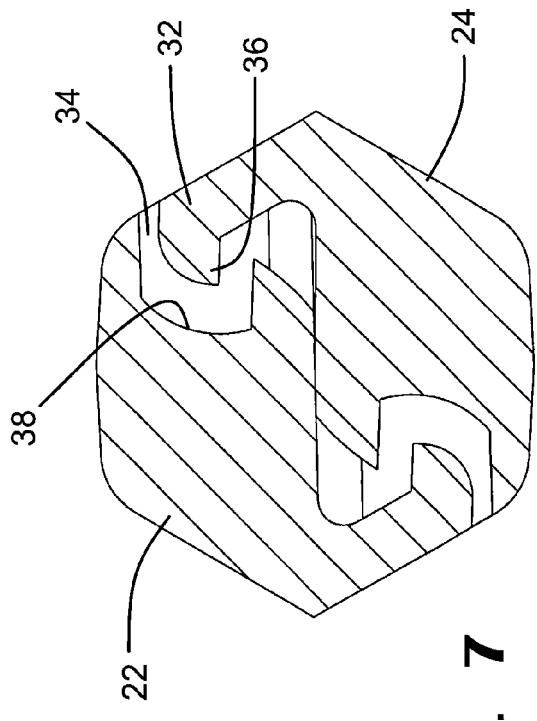
FIG. 7 is a cross sectional view through line 7-7 of FIG. 6.

As illustrated and best shown in FIGS. 6 and 7, the mechanical stop 26 includes a projection 28 extending downward from the first or upper handle portion 22 and extending into a slot 30 formed in the second or lower handle portion 24. In this embodiment, a projection 32 is also formed on the second or lower handle portion 24 that extends upward into a slot 34 formed in the first or upper handle portion 22. In operation, when forces are applied to the handle portions 22, 24 to cause relative movement of the handle portion 22 towards the tip 12 (to the left in FIG. 6) and the handle portion 24 away from the tip (to the right in FIG. 6), such movement is allowed until an edge of the projection 28 abuts an end of the slot 30 and an edge of the projection 32 abuts an end of the slot 34.

Referring now to FIG. 7, it can be seen that in the preferred embodiment illustrated, the projection 32 on the second handle portion 24 includes a radially inwardly extending lip 36 that is snap fit into a complementary groove 38 formed within the slot 34 of the first handle portion 22. In this manner, the lip 36 and the groove 38 cooperate to prevent relative movement between the first and second handle portions 22, 24 of the respective actuator arms 12, 14 away from one another in a radial direction, while still allowing relative movement between the first and second actuator arms 12, 14 in the direction of the axial length of the curette 10. The projection 28 and slot 30, as well as the projections and slots of the remaining mechanical stops, are formed with cooperating lips and grooves in the same manner.

To assist with actuation of the articulating ear curette of the invention, one or both of the first and second actuator arms 12, 14 may be provided with finger grips. In the preferred, illustrated embodiment, a first pair of spaced projections 40, 42 are provided on the first actuator arm 14 that extend away from the second actuator arm 16, while and a second pair of spaced projections 44, 46 are provided on the second actuator arm 16 that extend away from the first actuator arm 14. These projections provide opposed, first and second finger grips, facilitating the application of opposed axial forces to the first and second actuator arms 14, 16 by a user.

Figure 5:
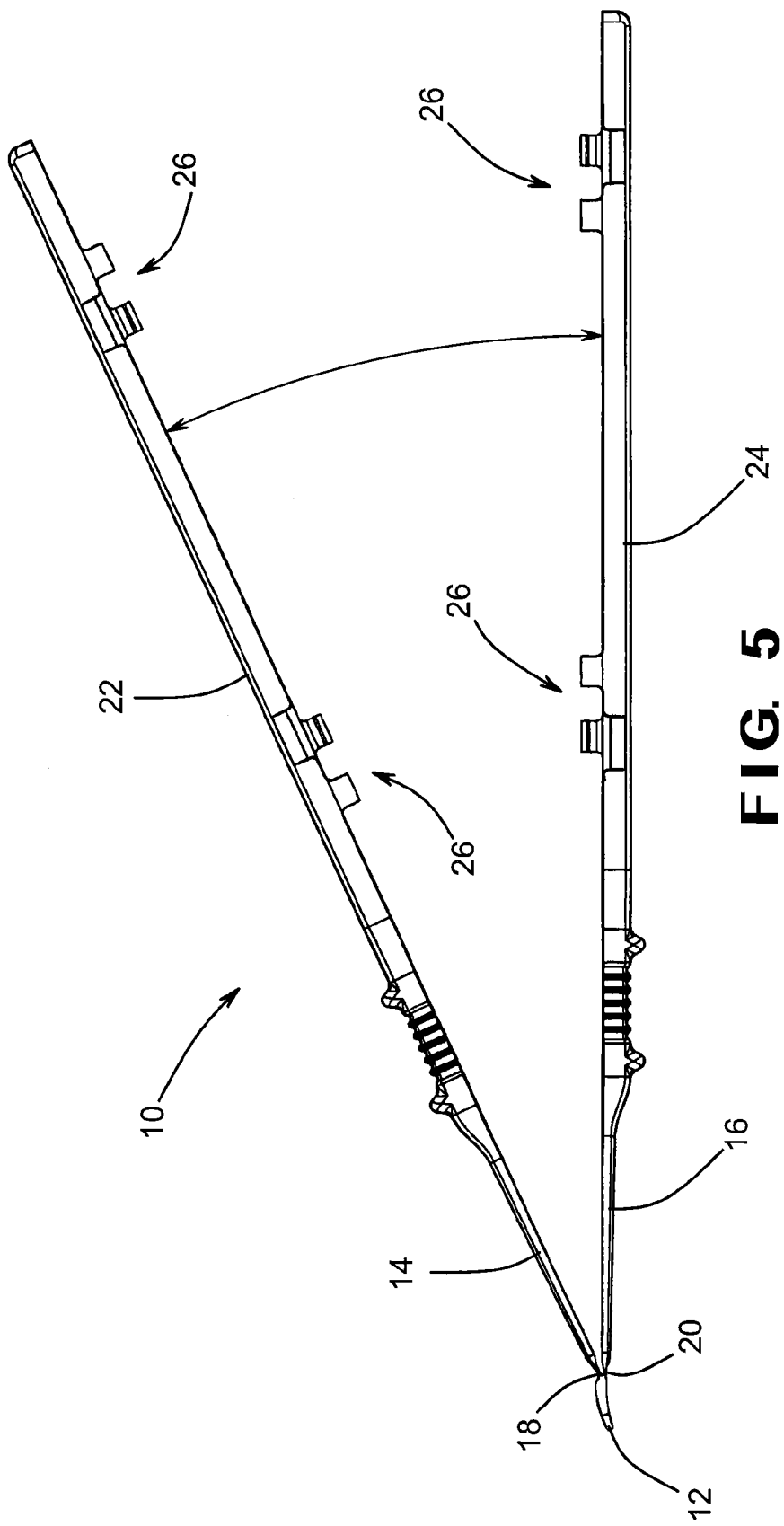
FIG. 5 is a side view of the curette of FIG. 1 prior to assembly.

Preferably, the curette of the invention is fabricated by molding the tip 12 and the first and second actuator arms 14, 16 to form a single, monolithic piece from a polymeric material possessing the desired strength and flexibility. Suitable polymer materials may be comprised of polyethylene, polypropylene, styrene-butadiene copolymers, and the like, as examples. The molded, unassembled curette 10 is shown in FIG. 5. To assemble the curette 10, the first and second handle portions 22 and 24 are simply brought together so that each of the projections formed on one of the handle portions is aligned with the corresponding slot formed in the other of the handle portions. The handle portions 22, 24 are then forced toward one another until each of the lips of the various mechanical stops has been snap fit into its corresponding groove.

Figure 2:
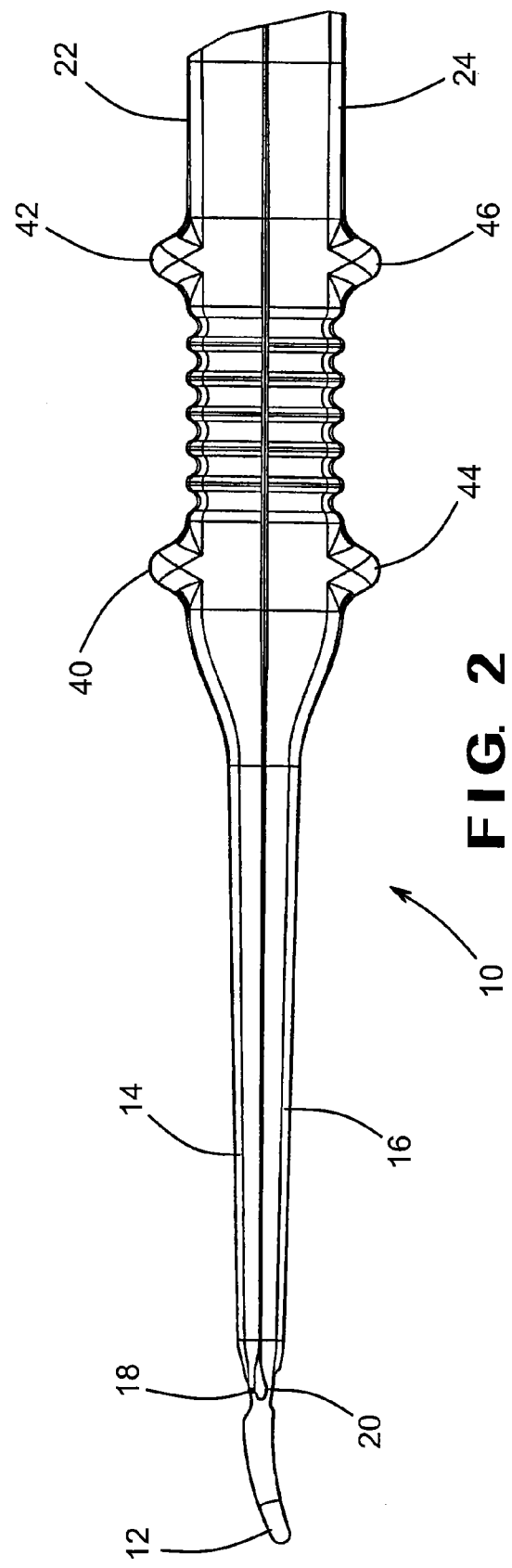
FIG. 2 is an enlarged view of an end portion of the curette shown in FIG. 1.

Once assembled, as best seen in FIGS. 2 and 4, the hinge 18, the upper hinge point as shown in the drawing figures, and the hinge 20, the lower hinge point as shown in the drawing figures, are longitudinally aligned with each other but are radially off-set from each other so that force applied to one hinge will cause the other hinge to deflect from the linear or longitudinal axis of the curette 10. As described above, force is transmitted to the hinge point by the associated actuator arm, which in turn is really an extension of the device handle, either upper or lower. In the preferred embodiment of the device, force is applied to the first or upper actuator arm 14 causing it to slide forward towards the tip 12. The force of sliding the upper handle/actuator arm is transmitted to the upper hinge point 18 that in turn forces the tip to deflect downward, flexing on the lower hinge point 20. This causes the curette tip 12 to flex downward relative to the linear or longitudinal axis of the curette 10. To straighten the curette tip 12, the user simply slides the first or upper actuator arm 14 rearward relative to the lower or second actuator arm 16, reversing the force vector on the upper hinge point 18 and straightening the tip 12.

In use of the curette 10, an otoscope is typically employed initially to determine the presence and location of wax or foreign body in the ear canal. The user holds the curette 10 in a pencil-like grip, using the two handle portions 22, 24 as he would the handle of a conventional ear curette. The tip 12 of the articulating curette 10 is then advanced past the occluding material. Once past the obstruction, the user simply slides his/her thumb, typically positioned between the projections 44 and 46, relative to his/her finger positioned between the projections 40 and 42, causing the two actuating arms 14, 16 of the curette 12 to slide relative to each other along the longitudinal axis of the curette. As they do so, the lever action produced causes the tip 12 of the curette 10 to bend down relative to the axis of the curette 10. While keeping the tip flexed, the user is then able to remove the curette from the ear canal, removing any wax or foreign objects.

In accordance with the provisions of the patent statutes, the invention has been described in what is considered to represent its preferred embodiments. However, it should be noted that the invention could be practiced otherwise than as specifically illustrated and described without departing from its spirit or scope.

What is claimed is:
1. A method of removing cerumen or a foreign body from an ear canal, comprising:
   providing an ear curette comprised of a curette tip connected to first and second actuator arms, the tip being connected to the first actuator arm through a first molded-in living hinge and the tip being connected to the second actuator arm through a second molded-in living hinge;

introducing the curette tip into the ear canal;

actuating the ear curette by forcing the first and second actuator arms in opposite directions, thereby causing movement of the curette tip about the first and second living hinges, the curette tip engaging at least a portion of the cerumen or the foreign body in the ear canal; and withdrawing the curette tip and the at least a portion of the cerumen or the foreign body from the ear canal.

2. The method of claim 1, wherein the first and second actuator arms are actuated by being forced to slide relative to the long axis of the curette to cause movement of the tip.

3. The method of claim 1, wherein the first and second actuator arms are forced to slide in opposite directions relative to the long axis of the curette until further such relative movement is prevented by at least one mechanical stop.

4. The method of claim 1, wherein the first and second hinges are longitudinally aligned with each other but radially off-set from each other so that force applied to one of the first and second hinges will cause the other of the first and second hinges to deflect from the long axis of the curette.

5. The method of claim 1, wherein the first molded-in living hinge is formed as a thin web between the tip and the first actuator arm and the second molded-in living hinge is formed as a thin web between the tip and the second actuator arm.

* * * * *